US010639131B2

(12) United States Patent
Yamagawa et al.

(10) Patent No.: US 10,639,131 B2
(45) Date of Patent: May 5, 2020

(54) RESIN BLOCK AND PROCESS FOR PRODUCING THE SAME

(71) Applicant: Tokuyama Dental Corporation, Tokyo (JP)

(72) Inventors: Junichiro Yamagawa, Tokyo (JP); Tomonao Shimizu, Tokyo (JP); Yuko Nagasawa, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 123 days.

(21) Appl. No.: 15/770,220

(22) PCT Filed: Oct. 25, 2016

(86) PCT No.: PCT/JP2016/081614
§ 371 (c)(1),
(2) Date: Apr. 23, 2018

(87) PCT Pub. No.: WO2017/073572
PCT Pub. Date: May 4, 2017

(65) Prior Publication Data
US 2018/0303587 A1    Oct. 25, 2018

(30) Foreign Application Priority Data
Oct. 26, 2015    (JP) .................................. 2015-210049

(51) Int. Cl.
*A61C 13/00*    (2006.01)
*A61C 13/09*    (2006.01)
(Continued)

(52) U.S. Cl.
CPC ...... *A61C 13/0022* (2013.01); *A61C 13/0004* (2013.01); *A61C 13/081* (2013.01);
(Continued)

(58) Field of Classification Search
CPC ............ A61C 13/0022; A61C 13/0004; A61C 13/081; A61C 13/087; A61C 13/09;
(Continued)

(56) References Cited

U.S. PATENT DOCUMENTS 5,990,195 A    11/1999    Arita
7,255,562 B2    8/2007    Rusin
(Continued)

FOREIGN PATENT DOCUMENTS

JP    10323353 A    12/1998
JP    2003529386 A    10/2003
(Continued)

OTHER PUBLICATIONS

International Search Report dated Jan. 10, 2017 filed in PCT/JP2016/081614.

*Primary Examiner* — Stella K Yi
(74) *Attorney, Agent, or Firm* — Rankin, Hill & Clark LLP (57) ABSTRACT

A resin block that can be favorably used for obtaining dental prosthetics through the milling work, containing very little voids, having excellent property for being cut, exhibiting excellent appearance and mechanical strength, and without permitting the formation of defective products. The resin block contains a thermoplastic resin having a fluidizing temperature in a range of 310 to 500° C. and inorganic particles in an amount of 30 to 150 parts by mass per 100 parts by mass of said thermoplastic resin. The inorganic particles are at least one kind of inorganic oxide particles selected from the group consisting of silica particles, silica composite particles of silica and other metal oxides, titania particles, and titania composite particles of titania and other metal oxides. The resin block has a thick portion of a
(Continued)

thickness of at least not less than 5 mm, and does not contain any void whose length is not less than 1.0 mm.

7 Claims, 5 Drawing Sheets

(51) Int. Cl.

| | |
|---|---|
| *C08J 5/00* | (2006.01) |
| *A61C 13/087* | (2006.01) |
| *C08L 101/00* | (2006.01) |
| *C08K 3/00* | (2018.01) |
| *A61C 13/20* | (2006.01) |
| *A61K 6/831* | (2020.01) |
| *A61K 6/844* | (2020.01) |
| *A61K 6/853* | (2020.01) |
| *A61K 6/891* | (2020.01) |
| *A61C 13/08* | (2006.01) |
| *B29C 45/00* | (2006.01) |
| *C08K 3/22* | (2006.01) |
| *C08K 3/36* | (2006.01) |
| *B29K 101/12* | (2006.01) |
| *B29K 105/16* | (2006.01) |
| *B29L 31/00* | (2006.01) |

(52) U.S. Cl.
CPC .............. *A61C 13/087* (2013.01); *A61C 13/09* (2013.01); *A61C 13/206* (2013.01); *A61K 6/831* (2020.01); *A61K 6/844* (2020.01); *A61K 6/853* (2020.01); *A61K 6/891* (2020.01); *B29C 45/0001* (2013.01); *B29C 45/0055* (2013.01); *C08J 5/00* (2013.01); *C08K 3/00* (2013.01); *C08K 3/22* (2013.01); *C08K 3/36* (2013.01); *C08L 101/00* (2013.01); *B29K 2101/12* (2013.01); *B29K 2105/16* (2013.01); *B29L 2031/7532* (2013.01); *C08J 2371/10* (2013.01); *C08K 2003/2241* (2013.01)

(58) Field of Classification Search
CPC ..... A61C 13/206; B29C 43/00; B29C 43/003; B29C 43/34; B29C 2043/3444; B29C 43/361; B29C 45/0053; B29C 45/56; B29C 45/561; B29C 45/564; B29C 2045/5665
See application file for complete search history.

(56) References Cited

U.S. PATENT DOCUMENTS

| | | | |
|---|---|---|---|
| 7,845,947 | B2 | 12/2010 | Rusin |
| 8,317,516 | B2 | 11/2012 | Rusin |
| 2002/0074675 | A1 | 6/2002 | Meyertholen |
| 2003/0157357 | A1 | 8/2003 | Rusin |
| 2013/0172441 | A1 | 7/2013 | Takahata |
| 2017/0165152 | A1* | 6/2017 | Eckert .................. A61K 6/083 |

FOREIGN PATENT DOCUMENTS

| | | |
|---|---|---|
| JP | 2004516066 A | 6/2004 |
| JP | 2014152150 A | 8/2014 |
| JP | 2014161440 A | 9/2014 |
| JP | 201598450 A | 5/2015 |
| WO | 2012042911 A1 | 4/2012 |

* cited by examiner

RESIN BLOCK AND PROCESS FOR PRODUCING THE SAME

TECHNICAL FIELD

This invention relates to a resin block having little voids, excellent appearance and mechanical strength. More specifically, the invention relates to a resin block that is suited for use as a prosthetic in the field of dental treatment and that can be favorably used as a restorative material upon being subjected to the milling work by using a CAD/CAM (computer aided designing•manufacturing) system. The invention, further, relates to a process for producing the resin block.

BACKGROUND ART

Super engineering plastics have been used in a wide range of applications in such fields as electric•electronic engineering, aircraft and space engineering, automotive industries, medicines and in industries in general. Among the super engineering plastics, in particular, an polyaryletherketone has been expected because of its excellent chemical and physical properties. The super engineering plastics featuring a variety of advantages, however, are also accompanied by such problems that they bend easily and are easily worn out. To improve these problems, there has been generally known a method of obtaining the resin as a composite material by adding a filler thereto.

Here, the restorative work in the dental treatment has heretofore been carried out by either filling a dental composite resin or by using a prosthetic material such as inlay, crown or bridge.

The latter method consists of the steps of forming a cavity or forming an abutment tooth, forming impression, forming a gypsum model and preparing a prosthetic, and, thereafter, adhering and joining the prosthetic to the cavity or the abutment tooth. When the prosthetics are made of a metal as represented by a gold-silver-palladium alloy, there is representatively employed a complex mold casting method called lost wax casting.

As described above, preparation of prosthetics has, so far, required a complex and minute work necessitating skillful dental technicians and a lot of working time, i.e., necessitating a tremendous amount of time and cost. Moreover, use of the above alloy is accompanied by such problems as metal allergy, depletion of resources, fluctuation in price and so on.

On the other hand, recent development in the CAD/CAM systems is now making it possible to prepare precise dental prosthetics in short periods of time and in large quantities relying on the milling work by utilizing the above systems. There have now been placed in the market CAD/CAM systems for designing and preparing the prosthetics.

The milling work based on the CAD/CAM system can deal with the works or blocks of such shapes as rectangular parallelepiped, cylinder, disc, etc. As the material for constituting the blocks, ceramics were, first, considered accompanied, however, by the problems in regard to the workability due to their high hardness, damage to the natural teeth after the prosthetic has been fitted and high prices. In recent years, therefore, study has been forwarded to develop blocks comprising inorganic filler materials and resins.

In the resin materials for blocks developed thus far, however, the resin components that served as base materials were all thermosetting acrylic resins (cured polymers of acrylic monomers) (patent documents 1, 2 and 3). Therefore, the resin materials were poor in their mechanical strength and were not strong enough for use as prosthetics for true molar teeth or bridges on where high pressures of occlusion were subject to be applied.

On the other hand, attempts have been made to use a super engineering plastic as a dental material that needs a large mechanical strength. However, nothing has yet been disclosed concerning the problems that might occur during the milling work of the above material. In particular, nothing has been brought into attention concerning the occurrence of voids when the dental material is melt-formed or concerning the effects of voids upon the appearance of the formed body, defects in the formed body, mechanical strength or workability of milling (patent document 4).

PRIOR ART DOCUMENTS

Patent document 1: International Laid-Open No. 2012/042911
Patent document 2: JP-A-10-323353
Patent document 3: JP-W-2003-529386
Patent document 4: JP-A-2014-152150

OUTLINE OF THE INVENTION

Problems that the Invention is to Solve

Voids stand for gap-like defects that occur inside the product. Namely, when a thermoplastic resin or a composition that contains it is cooled from a molten state down to a solid state, the portions of the thermally inflated resin are, first, cooled and solidified as they come in contact with the open air or the mold. That is, a contraction of the volume of the whole formed body appears as vacuum gaps inside the formed body. Specifically, the voids occur easily in thick products due to the mechanism of occurrence. Further, when a crystalline thermoplastic resin is used, the ratio of contraction becomes large due to the contraction that accompanies the crystallization, and voids occur more easily.

The present inventors have paid attention to that with the conventional melt-forming methods, voids are prone to occur due to the thermal contraction at the time of forming thick bodies and that the presence of voids affects the appearance, mechanical strength and workability of milling of the formed body and, further, results in the formation of defective products. The inventors have, therefore, discovered that the occurrence of voids can be suppressed if a particular compressive operation is carried out in forming the blocks but before the blocks are solidified, and have thus completed the invention.

Means for Solving the Problems

According to the present invention, there is provided a resin block that contains a thermoplastic resin having a fluidizing temperature in a range of 310 to 500°C and inorganic particles in an amount of 30 to 150 parts by mass per 100 parts by mass of the thermoplastic resin, and that can be used as a material for producing a dental prosthetic through the milling work, wherein:

the inorganic particles are at least one kind of inorganic oxide particles selected from the group consisting of silica particles, silica composite particles of silica and other metal oxides, titania particles, and titania composite particles of titania and other metal oxides;

the resin block has a thick portion of a thickness of at least not less than 5 mm; and the resin block does not contain any void whose length is not less than 1.0 mm.

In the above resin block, it is desired that:
1) The thermoplastic resin is a crystalline thermoplastic resin;
2) The thick portion has a thickness of 10 to 50 mm;
3) The resin block does not contain any void whose length is not less than 0.2 mm; and
4) The milling work is executed by using a CAD/CAM (computer aided design•manufacturing) system.

According to the present invention, there is further provided a process for producing a resin block that contains a thermoplastic resin and inorganic particles, that does not contain any void whose length is not less than 1.0 mm, that has a thick portion of a thickness of at least not less than 5 mm, and that can be used as a material for producing a dental prosthetic through the milling work:

by providing a thermoplastic resin composition that contains a thermoplastic resin having a fluidizing temperature in a range of 310 to 500° C. and at least one kind of inorganic oxide particles selected from the group consisting of silica particles, silica composite particles of silica and other metal oxides, titania particles, and titania composite particles of titania and other metal oxides in an amount of 30 to 150 parts by mass per 100 parts by mass of the thermoplastic resin, and comprising the steps of:

injecting and filling a melt of the thermoplastic resin composition in a cavity of an injection-molding machine that has a projection mechanism;

exerting a pressure on the thermoplastic resin composition;

pushing a projecting member into one side surface of the cavity filled with the thermoplastic resin composition over a contact area of not more than 50% on the basis of the area of the whole one side surface before the thermoplastic resin composition is completely solidified; and taking out the thermoplastic resin composition after it has been cooled down.

In the above process for producing the resin block, it is desired that a portion in one side surface in the cavity with which the projecting member comes in contact is formed being protruded toward the outer side of the cavity, and that the projecting member is put onto the protruded portion and is so pushed that the side surface of the cavity becomes nearly flat.

According to the present invention, further, there is provided a process for producing a resin block that contains a thermoplastic resin and inorganic particles, that does not contain any void whose length is not less than 1.0 mm, that has a thick portion of a thickness of at least not less than 5 mm, and that can be used as a material for producing a dental prosthetic through the milling work:

by providing a thermoplastic resin composition that contains a thermoplastic resin having a fluidizing temperature in a range of 310 to 500° C. and at least one kind of inorganic oxide particles selected from the group consisting of silica particles, silica composite particles of silica and other metal oxides, titania particles, and titania composite particles of titania and other metal oxides in an amount of 30 to 150 parts by mass per 100 parts by mass of the thermoplastic resin, and comprising the steps of:

injecting and filling a melt of the thermoplastic resin composition in a cavity of an injection-molding machine that has a projection mechanism;

exerting a pressure on the thermoplastic resin composition;

pushing a projecting member into one side surface of a compression chamber that has a pushing portion, over a contact area of not more than 50% on the basis of the area of the whole one side surface before the thermoplastic resin composition is completely solidified, the compression chamber having a volume which is 0.2 to 80% the volume of the cavity and, further, having a space continuous to the interior of the cavity; and taking out the thermoplastic resin composition after it has been cooled down.

In the process for producing the resin block, it is desired that:
1) The thermoplastic resin is a crystalline thermoplastic resin;
2) The resin block does not contain any void whose length is not less than 0.2 mm;
3) The thick portion has a thickness of 10 to 50 mm; and
4) The milling work is executed by using a CAD/CAM (computer aided design•manufacturing) system.

Effects of the Invention

Owing to the features attained by the process of production, the resin block of the present invention contains very little voids. Therefore, the resin block exhibits excellent appearance when it is cut, can be cut very favorably, and features excellent mechanical strength such as compression strength, tensile strength and flexural strength, eliminating the probabilities of producing defective products.

Concretely speaking, there is not substantially contained any void whose length is not less than 1.0 mm and, preferably, not less than 0.2 mm. This, therefore, brings about the following features.
1) The body after having been cut exhibits a strength inherently possessed by the resin block, i.e., exhibits improved quality.
2) The body after having been cut exhibits no defective appearance since no void is exposed.
3) The resin block is prone to contain more voids as the size of the resin block increases. The invention, however, permits the resin block to be designed in a large size and to be applied to forming larger bodies (prosthetics) through the milling work.
4) Prevents the breakage that originates from the voids and eliminates the occurrence of defect in the products.
5) The product (resin block) by itself acquires an increased strength and becomes less liable to be broken during the transport.
6) Despite the cut-worked body is worn out after the use, no void appears in the surface and the appearance is not impaired.
7) Voids may often be contained in a sprue. The body, however, is prevented from splitting off despite the load is exerted by the milling machine during the milling work.
8) Despite the milling machine may exert the load unevenly on the material, it is allowed to prevent a decrease in the precision for milling the body (prosthetic).

Therefore, a very precise dental prosthetic can be prepared through the milling work based on the CAD/CAM system, and can be favorably used for molar teeth that receive a large pressure of occlusion and for bridges.

As a result, there can be provided dental prosthetics efficiently, maintaining good productivity and inexpensively to substitute for the metal prosthetics that were thus far formed by using alloys. Moreover, the resin blocks can be produced by the injection-molding maintaining a higher efficiency than that based on the extrusion forming, and offering advantages in the productivity and cost, particularly, in the field of dental treatment.

MODES FOR CARRYING OUT THE INVENTION

[Resin Block]

The resin block of the present invention contains a thermoplastic resin having a fluidizing temperature in a range of 310 to 500° C. and inorganic particles of a specific inorganic oxide in an amount of 30 to 150 parts by mass per 100 parts by mass of the resin. The resin block has a thick portion of a thickness of at least not less than 5 mm and does not contain any void whose length is not less than 1.0 mm.

The resin block having a thick portion of a thickness of at least not less than 5 mm and, preferably, 10 to 50 mm, makes it possible to prepare a variety of dental prosthetics such as inlay, crown, bridge and the like.

There is no limitation on the shape of the resin block of the invention, and there may be selected any shape that would meet the object out of rectangular parallelepiped, cube, cylinder, disc, sphere and complex structures of a combination of various shapes. In the case of the rectangular parallelepiped and cubic shapes, the length of a side should be, preferably, in a range of 5 to 50 mm. In the case of the cylindrical and disc shapes, the diameter should be in a range of 90 to 110 mm and the thickness should be in a range of 5 to 50 mm. In the invention, the thickness of the thick portion is a thickness of a cubic resin block in the direction of thickness thereof. In case there exists a locally protruded portion such as rib or the like, the thickness includes the thickness of the locally protruded portion.

The resin block does not contain any void whose length is no less than 1.0 mm and, therefore, can be cut excellently. More than that, the body obtained from the resin block through the milling work features excellent appearance, mechanical strength such as high degree of durability against the stress and little strain when stress is exerted on it. Specifically, when there is no void whose length is not less than 0.2 mm, the above effects can be further improved.

In the invention, the voids stand for vacuum spaces formed in the resin block, i.e., stand for spaces having the longest diameters of not less than 0.2 mm.

Presence and lengths of voids are observed and measured by using an X-ray inspection apparatus. The X-ray radiographic apparatus has an X-ray source whose X-ray intensity is powerful enough to pass through the resin block which is the object. If the X-ray is powerful enough to pass through the sample differs depending on the thickness of the sample and permeability for X-rays, and, therefore, should be confirmed in advance. The voids can assume a variety of shapes depending on the method of forming. Generally, however, the voids may assume a spherical shape, a nearly spherical shape, an elliptic shape or a nearly elliptic shape. Whatever the shape is, the longest diameter of each void is regarded to be the "length" of the void.

In the case of the resin block that contains the inorganic particles of high aspect ratios, the voids may assume the form of mesh, stripes or fog. In any case, the resin block of the present invention does not substantially contain any void whose longest diameter is not less than 1.0 mm.

[(A) Thermoplastic Resin]

The base material that constitutes the resin block is a thermoplastic resin having a fluidizing temperature in a range of 310 to 500° C. The thermoplastic resin of this kind is, usually, called super engineering plastics and has a high degree of heat resistance and mechanical strength. The interior of an oral cavity is, at all times, exposed to a severe environment due to various loads such as temperature, humidity, stress, abrasion and foods. Use of a resin such as super engineering plastics as a base material, however, is desired from the standpoint of high degree of durability in severe environments.

However, the resin of this kind, usually, requires a high temperature before it is melted and fluidized. Therefore, the resin undergoes the thermal shrinkage due to a large temperature differential between the step of melting and the step of cooling and solidification, causing such a problem that voids easily develop in the thick body. The resin block of the present invention has a feature in the use of such a thermoplastic resin as the base material yet substantially containing no void. The prosthetic or the body obtained from resin block through the milling work, therefore, offers an advantage in appearance, i.e., no void is present in the surface thereof. Moreover, since no void is contained in the body that is obtained through the milling work, there are provided such effects as excellent workability for milling, durability and mechanical strength.

As a result, the body obtained through the milling work is strong against the load, deflects little, is not easily broken, and exhibits a high degree of durability even in severe environments. Therefore, the cut body can be effectively utilized as a dental prosthetic to substitute for the metal counterparts.

The resins having a fluidizing temperature of lower than 310° C. are basically poor in mechanical strength such as flexural strength. The resins having higher fluidizing temperatures, on the other hand, are desirable from the standpoint of mechanical strength. Here, however, the upper limit of 500° C. is determined from the practical standpoint such as selecting the material and easiness of availability. The fluidizing temperature is a temperature at which the resin is melted and becomes able to be transferred by screw. In the case of the crystalline thermoplastic resin, the fluidizing temperature is a temperature (usually, +5 to 100° C.) which is higher than a melting point thereof. In the case of the amorphous thermoplastic resin, the fluidizing temperature is a temperature (usually, +50 to 250° C.) which is higher than a glass transition point thereof. In the case of a crystalline thermoplastic resin, a preferred melting point is in a range of 330 to 390° C.

Described below are examples of the thermoplastic resins having the above-mentioned fluidizing temperatures.

Polysulfone resin: preferred fluidizing temperature, 330 to 400° C.

Polyethersulfone resin: preferred fluidizing temperature, 310 to 390° C.

Polyphenylenesulfide resin: preferred fluidizing temperature, 310 to 390° C.

Polyarylate resin: preferred fluidizing temperature, 310 to 390° C.

Polyetherimide resin: preferred fluidizing temperature, 340 to 430° C.

Liquid crystal polymer: preferred fluidizing temperature, 320 to 400° C.

Polyaryletherketone: preferred fluidizing temperature, 340 to 400° C.

Among these resins, a crystalline thermoplastic resin is preferably used from the standpoint of a high flexural strength and modulus of elasticity. An polyaryletherketone and a liquid crystal polymer are preferably used particularly from the standpoint of a large mechanical strength, resistance against the chemicals, water-proof property and resistance against being colored. From the standpoint of safety to the living body, the polyaryletherketone is preferred.

The polyaryletherketone is a general term of the resins of a structure in which a benzene ring is linearly coupled via an ether group and a ketone group as a bonding group. Specifically, the aromatic polyetherketone can be represented by a polyetherketone (PEK) having a basic linear structure in which an ether group and a ketone group are arranged alternatingly as bonding groups to bond a benzene ring to another benzene ring that are neighboring each other to constitute a linear main chain, a polyetheretherketone (PEEK) in which bonding groups are arranged in order of ether group •ether group•ketone group, a polyetherketoneketone (PEKK) in which bonding groups are arranged in order of ether group•ketone group•ketone group, a polyetheretherketoneketone (PEEKK) in which bonding groups are arranged in order of ether group•ether group•ketone group•ketone group, and a polyetheretherketoneketone (PEKEKK).

Among these polyaryletherketones, the aromatic polyetheretherketone is desired because of its excellent mechanical properties such as flexural strength and breaking energy. This resin has been placed in the market in the trade name of "PEEK" and, representatively, in the trade names of VESTAKEEP (Evonik) and VICTREX PEEK (Victrex).

As the liquid crystal polymer, there can be exemplified a totally aromatic polyester, a polyesteramide and an aromatic polyazomethine. Generally, there has been known a polycondensed product of an ethylene terephthalate, a phenol or a biphenol with a phthalic acid or a 2,6-hydroxynaphthoic acid with the parahydroxybenzoic acid as a basic structure. As the commercially available products, there can be exemplified VECTRA (Polyplasics) and SUMICASUPER LCP (SUMITOMO CHEMICAL).

As for the polysulfone resin, there have been placed in the market UDEL, RADEL, VERADEL (Solvay Advanced Polymers Co.) and ULTRASON (BASF Co.) as resins having aromatic rings and of which the fluidizing temperatures lying within a range specified by the present invention.

The molecular weight of the thermoplastic resin can be suitably selected giving, however, attention to the points described below. In general, mechanical properties tend to be improved with an increase in the molecular weight of the thermoplastic resin accompanied, however, by a decrease in the fluidity of the thermoplastic resin that is plasticized. Besides, it often becomes difficult to add much inorganic particles thereto. Moreover, as the fluidity of the plasticized thermoplastic resin decreases, an increased load is exerted on the production apparatus in the step of melt-kneading and in the step of injection molding that are carried out for producing the resin blocks, and it often becomes difficult to continue the production maintaining stability. However, the lower the fluidity of the thermoplastic resin, the higher the efficiency for kneading the thermoplastic resin and the inorganic particles together. It is, therefore, recommended to select the molecular weight of the thermoplastic resin to attain a balance among them.

The above thermoplastic resins have been placed in the market and can be selectively used to meet properties required for the object, e.g., by taking the molecular weight and the fluidity during the forming into consideration. The thermoplastic resins can be used in two or more kinds being suitably mixed together. Moreover, as required, any thermoplastic resins other than those described above can also be suitably used so far as they satisfy the requirement of the fluidizing temperature.

[(B) Inorganic Particles]

The resin block of the present invention contains inorganic particles. It is essential to blend the resin block with the inorganic particles to produce such effects that the cut body acquires an improved rigidity and deflects less; the cut body acquires an improved abrasion resistance; the tools are less stuck with the resin during the milling work and the milling efficiency is improved. When no inorganic particle is contained, the resin block exhibits low mechanical strength and rigidity, and cannot be used as a prosthetic for restoring the crowns.

The larger the amount of the inorganic particles that are contained, the higher the rigidity of the resin block and the less it deflects accompanied, however, by an increase in the probability of brittle fracture. The larger the amount of the inorganic particles that are contained, the larger the abrasion resistance accompanied, however, by an increase in the probability of abrasion of the counter material in the oral cavity. Moreover, the larger the amount of the inorganic particles that are contained, the higher the effect for suppressing the resin from sticking to the tools accompanied, however, by an increase in the abrasion of the milling tools.

From the standpoint of the step of forming such as injection molding, the inorganic particles that are contained much make it possible to decrease the amount of the resin component and decrease the thermal shrinkage. As a result, the occurrence of voids can be suppressed, which is desirable. Addition of the inorganic particles in an increased amount, however, results in a decrease in the fluidity of the resin and makes it difficult to obtain the effect for suppressing the occurrence of voids caused by the compression. That is, voids tend to occur easily.

By taking the above-mentioned points into account, it is necessary that the inorganic particles are contained in an amount of 30 to 150 parts by mass per 100 parts by mass of the thermoplastic resin (A).

As the inorganic particles, there are used silica particles, silica composite oxide particles of silica and other metal oxides, titania particles or titania composite oxide articles of titania and other metal oxides from the standpoint of rigidity and abrasion resistance of the resin block, improving the working efficiency by suppressing the resin from sticking, and less harm to the living body. Moreover, it is desired that the inorganic particles have a spherical shape, a nearly spherical shape or a lump shape so that sharp ends of the inorganic particles will not be exposed on the surface of the crown prosthetic that is obtained by milling the resin block.

It is desired that the inorganic particles have their surfaces rendered hydrophobic in order to improve the dispersion property thereof in the thermoplastic resin (A). There is no specific limitation on the treatment for rendering the surfaces to be hydrophobic, and any known method can be employed without limitation.

A representative surface-treating method will be the one that uses a silane coupling agent or a titanate type coupling agent as the hydrophobic property-imparting agent. The kind and amount of the coupling agent, and the method of treatment, can be suitably selected from the conventional methods.

[(C) Other Materials to be Added]

The resin block of the present invention contains the above-mentioned thermoplastic resin and inorganic particles as basic components. The resin block, however, can be further blended with an antistatic agent, an ultraviolet ray absorber, a pigment, a coloring agent and the like within ranges in which they do not impair the properties of the resin block.

[Process for Producing the Resin Block]

In the invention, the resin block is produced by the injection-molding method. The injection-molding method is capable of producing resin blocks of a high quality maintaining a high yield at low costs.

The injection-molding, in general, consists of heating the material fed from a hopper at a suitable temperature in a heating cylinder so as to be favorably plasticized, and injecting the plasticized material into a mold under the conditions of a predetermined temperature, pressure and rate. At this moment, the mold is maintained tightly fastened so will not be pushed open by the pressure of the material injected into the mold. The mold has a cavity of a shape nearly the same as the shape of the product to be formed, and is mounted on an injection-molding machine. Typically, the step of injection molding includes the step of melting, the step of metering, the step of injection, the step of exerting the holding pressure, the step of cooling and the step of taking out the formed product. Depending on the cases, other steps may be added, some of the steps may be omitted, or some of the steps may often be partly overlapped.

Though there is no particular limitation on the method of injection molding employed by the present invention, the method can be concretely described as follows:

1) The process for production comprising the steps of:

injecting and filling a melt of a thermoplastic resin composition in a cavity of an injection-molding machine that has a projection mechanism, the thermoplastic resin composition containing a thermoplastic resin having a fluidizing temperature in a range of 310 to 500° C. and at least one kind of inorganic oxide particles selected from the group consisting of silica particles, silica composite particles of silica and other metal oxides, titania particles, and titania composite particles of titania and other metal oxides in an amount of 30 to 150 parts by mass per 100 parts by mass of the thermoplastic resin (step of injection);

exerting a pressure on the thermoplastic resin composition (step of exerting the holding pressure);

pushing a projecting member into one side surface of the cavity filled with the thermoplastic resin composition over a contact area of not more than 50% on the basis of the area of the whole side surface before the thermoplastic resin composition is completely solidified (step of compression); and taking out the thermoplastic resin composition after it has been cooled down (step of cooling, step of taking out the formed body).

2) The process for production set forth in 1) above, wherein in the step of compression, a portion in one side surface in the cavity with which the projecting member comes in contact is protruded toward the outer side of the cavity, and the projecting member is put onto the protruded portion and is so pushed that the side surface of the cavity becomes nearly flat (step of compression).

3) The process for production set forth in 1) above, further comprising, as the step of compression, the step of pushing a projecting member into one side surface of a compression chamber that has a push portion, over a contact area of not more than 50% on the basis of the area of the whole side surface, the compression chamber having a volume which is 0.2 to 80% the volume of the cavity and, further, having a space continuous to the interior of the cavity (step of compression).

In the process for producing the resin block of the present invention, it is important that the molten thermoplastic resin composition is injected and filled in the cavity of the mold and, thereafter, the compression operation is executed to, further, exert a pressure on the thermoplastic resin composition under specific conditions before the thermoplastic resin composition is completely solidified after the holding pressure has been exerted or while exerting the holding pressure.

The compression operation is not limited to the one that pushes the projecting member into the side surface of the cavity. The compression operation may also be carried out by separately providing a compression chamber having a pushing portion that has a space continuous to the interior of the cavity and a specific volume, and pushing the projecting member into the side surface of the compression chamber that has the pushing portion. Details will be described later.

As a result, the resin block that is obtained suppresses the occurrence of voids, and excels not only in its milling workability but also that the cut body thereof exhibits favorable appearance and mechanical strengths such as flexural strength and rigidity, which are the features inherent in the resin materials.

[Preparation of the Thermoplastic Resin Composition]

The essential components of the invention and other additives used as required are mixed together in advance to prepare a thermoplastic resin composition. The composition which is the starting material is then injection-molded into the resin block.

There is no specific limitation on the method of preparing the thermoplastic resin composition. Typically, there can be employed a dry-blending method that uses a blender or the Henschel mixer, or a melt-blending method that uses an extruder, the Banbury mixer or a kneader, followed by pelletization.

There is no specific limitation, either, on the order of mixing; i.e., the whole components may be mixed together simultaneously, or may be mixed together stepwise.

[Step of Injection]

The step of injection molding in the production process of the present invention is for injecting and filling the melt of the thermoplastic resin composition in the cavity.

Any methods can be used for melting and injection-filling the thermoplastic resin composition; i.e., any known methods, apparatus and instruments can be used. Qualities of the formed body can be affected by various conditions such as a temperature that is set, melting temperature, metering, duration for metering, feeding rate, revolving speed of the screw, setting the advancing amount of the screw, back pressure, injection rate, injection pressure, cushioning amount, position of completing the metering, suck back, mold temperature, setting the vent, etc. These factors, however, are general events in the injection molding. Therefore, optimum factors should be suitably selected and set in determining the injection-filling conditions.

[Step of Exerting the Holding Pressure]

In the step of exerting the holding pressure in the production process of the present invention, the pressure is exerted on the thermoplastic resin composition filled in the cavity. The holding pressure can be exerted by any known method using any apparatus or equipment. Usually, the pressure of injection is continuously held, and the pressure is exerted on the resin in the cavity from the injection portion via the molten thermoplastic resin composition. In this state, the thermoplastic resin composition is in the molten state. Therefore, by further pushing the molten resin composition into the cavity, it is make possible to avoid the lack of filling, loss of surface of the formed body and to suppress the voids.

Qualities of the formed body can be affected by various conditions such as the holding pressure, timing for switching the holding pressure, duration for applying the holding pressure and duration for sealing the gate. These factors, however, are general events in the injection molding. Therefore, optimum factors should be suitably selected and set in determining the conditions related to the holding pressure.

[Step of Compression]

In the step of compression in the production process of the present invention, a compression operation is executed to exert a further pressure by a special means on the thermoplastic resin composition under specific conditions before the thermoplastic resin composition is completely solidified. In this case, the preceding step of exerting the holding pressure may have been continued.

Concretely speaking, there can be employed an operation for pushing a projecting member into one side surface of the cavity filled with the thermoplastic resin composition over a contact area of not more than 50% on the basis of the area of the whole side surface before the thermoplastic resin composition is completely solidified.

There is no limitation on the projecting member provided it is capable of compressing the thermoplastic resin composition by the pushing operation. Namely, a projecting compression mechanism may be installed on the injection-molding machine, or the projecting compression mechanism may be installed on the mold as shown in FIGS. 1 and 2.

It is essential that the contact area of when the projecting member is pushed in is not more than 50% on the basis of the area of the side surface on where the pushing portion is present. If the projecting member is pushed in to compress over the area of not less than 50%, then the effect is not sufficient for suppressing the occurrence of voids. The cause is presumed to be as described below though it has not been clarified yet.

Figure 1:
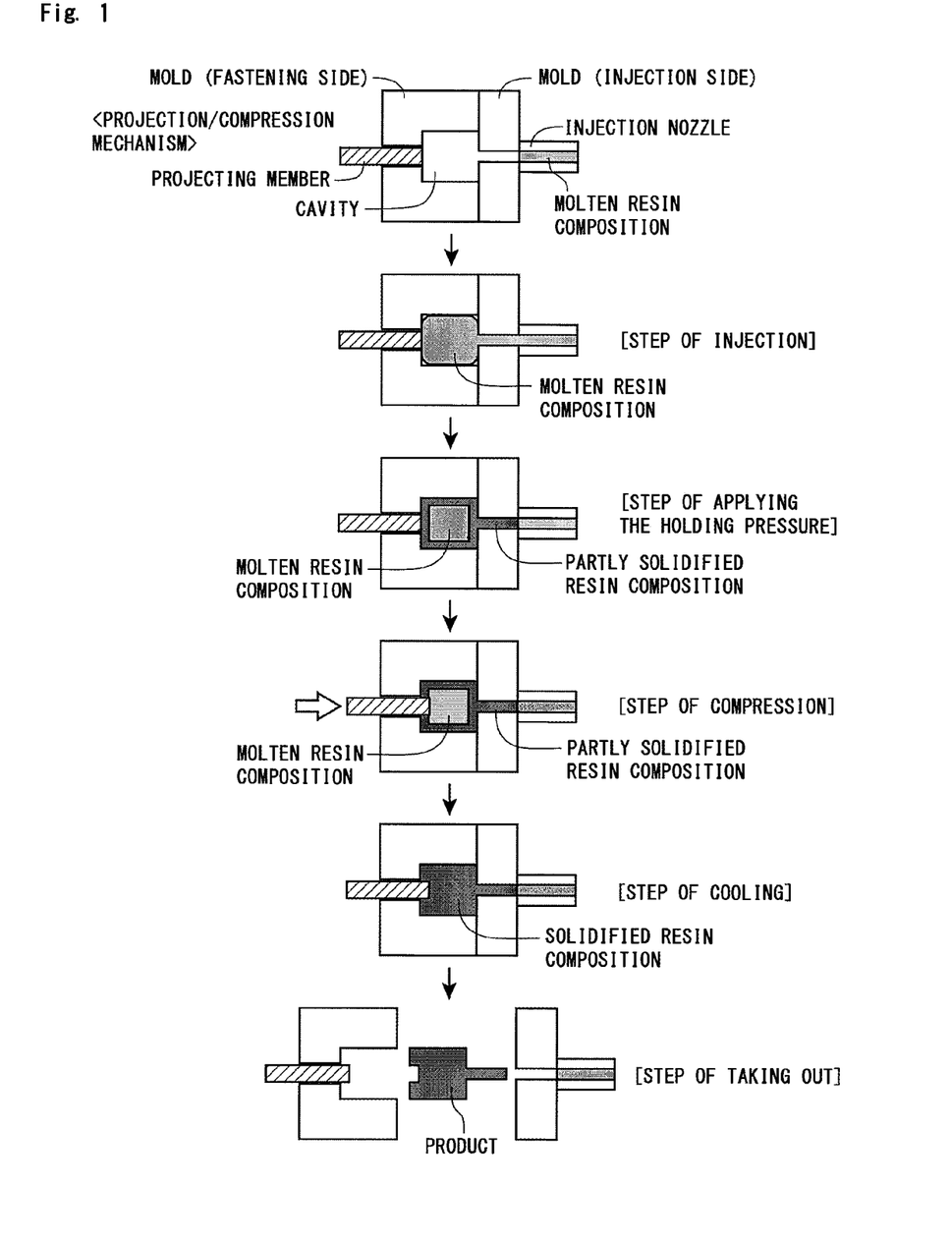
FIG. 1 It is a schematic view illustrating the steps of production that executes the compression operation by pushing a projecting member into a side surface of a cavity.
Figure 2:
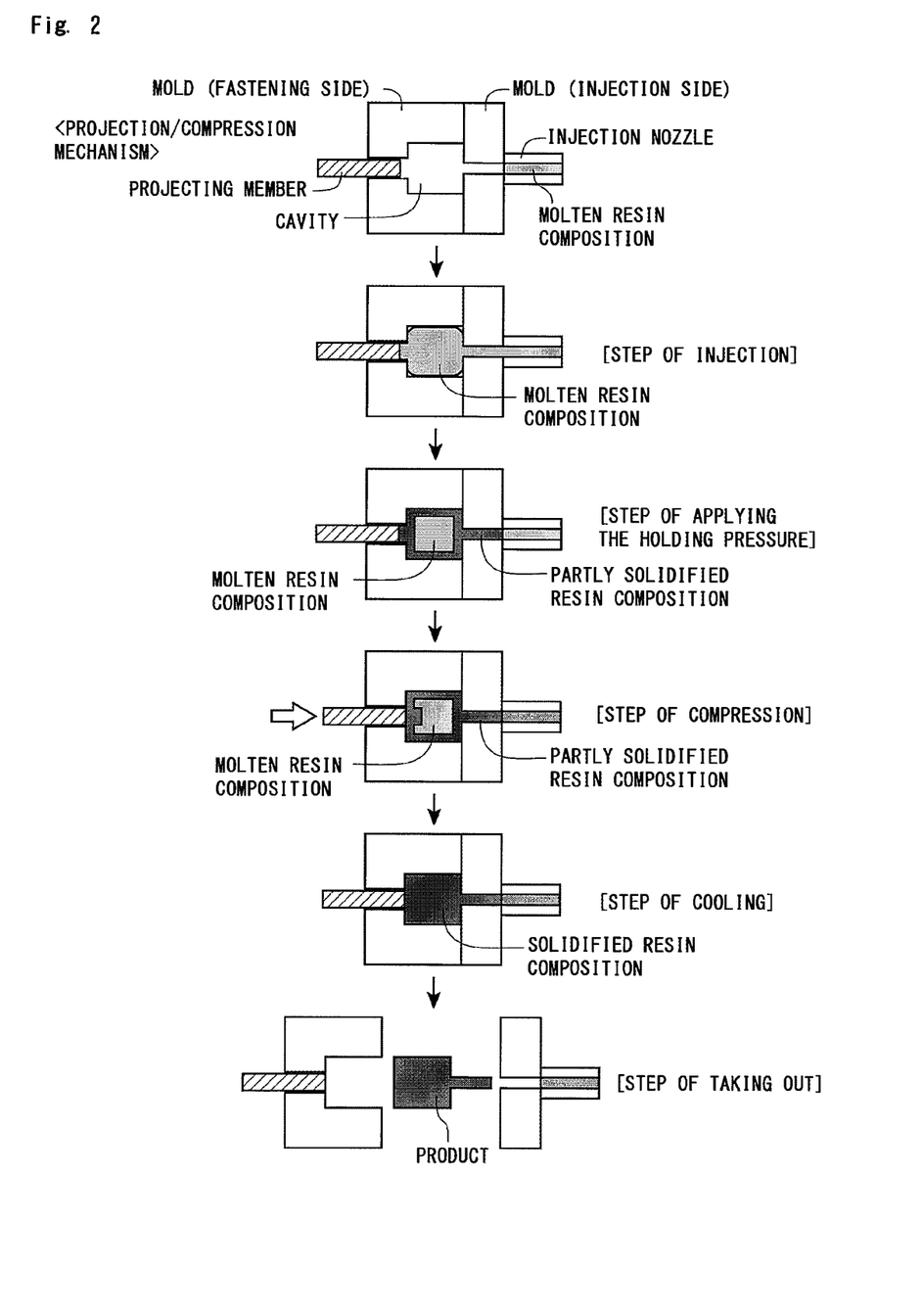
FIG. 2 It is a schematic view illustrating the steps of production that executes the compression operation by pushing the projecting member onto a protruded portion by using a cavity (mold) that is forming a portion protruded toward the outer side of the cavity.
Figure 3:
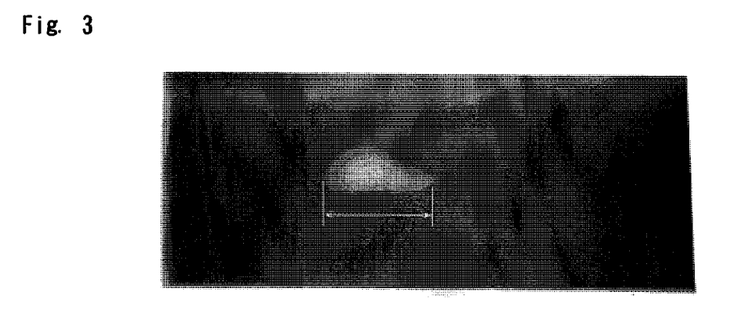
FIG. 3 It is a photograph showing a void and its maximum diameter in a resin block obtained in Comparative Example 1 as inspected by using the X-rays.
Figure 4:
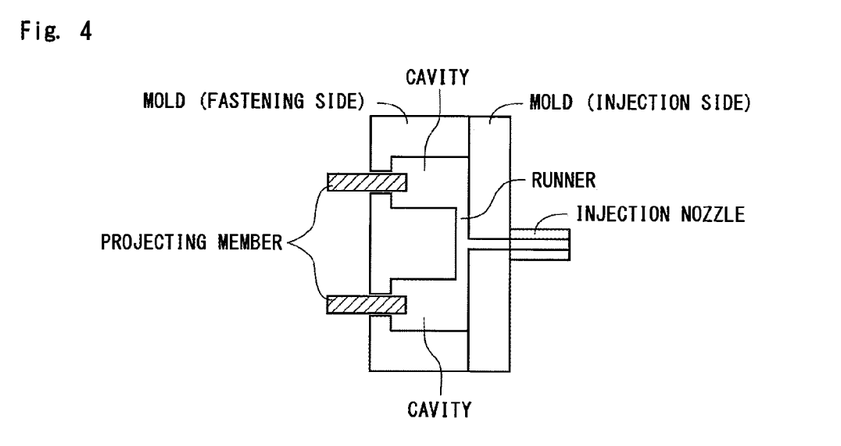
FIG. 4 It is a schematic view of an embodiment that has a plurality of cavities and executes the pushing operation for the cavities.

Referring to the steps of compression shown in FIGS. 1 and 2, the thermoplastic resin composition filled in the cavity is gradually solidified from the outer circumferential portion close to the surface of the mold toward the interior thereof. In the step of compression, therefore, there exists being mixed together the molten thermoplastic resin composition that has not been completely solidified and the thermoplastic resin composition that is cooled already and is solidifying in the outer circumferential portion. If the contact area is large, the thermoplastic resin composition that has started solidifying exists much in the outer circumferential portion in the direction in which the projecting member is pushed in. As a result, the compression resistance becomes so great that the pushing effect is not obtained to a sufficient degree. It is, therefore, desired that the contact area is not more than 30% but is not less than 1% from the standpoint of effectively suppressing the occurrence of voids.

There is no specific limitation in the direction of projection. It is, however, desired that the direction of projection is just opposite to the direction in which the thermoplastic resin composition is filled from the standpoint of efficiently realizing the effect of compression by pushing, easy design of the apparatus and simplicity of the mechanisms.

The pushing portion may be present in one place or in a plurality of places. When they are present in a plurality of places, the plurality of portions may be present on one side surface, or each portion may be present on the plurality of side surfaces. They can be arbitrarily selected depending on the shape of the resin block that is produced or the pressure exerted at the time of pushing.

Figure 7:
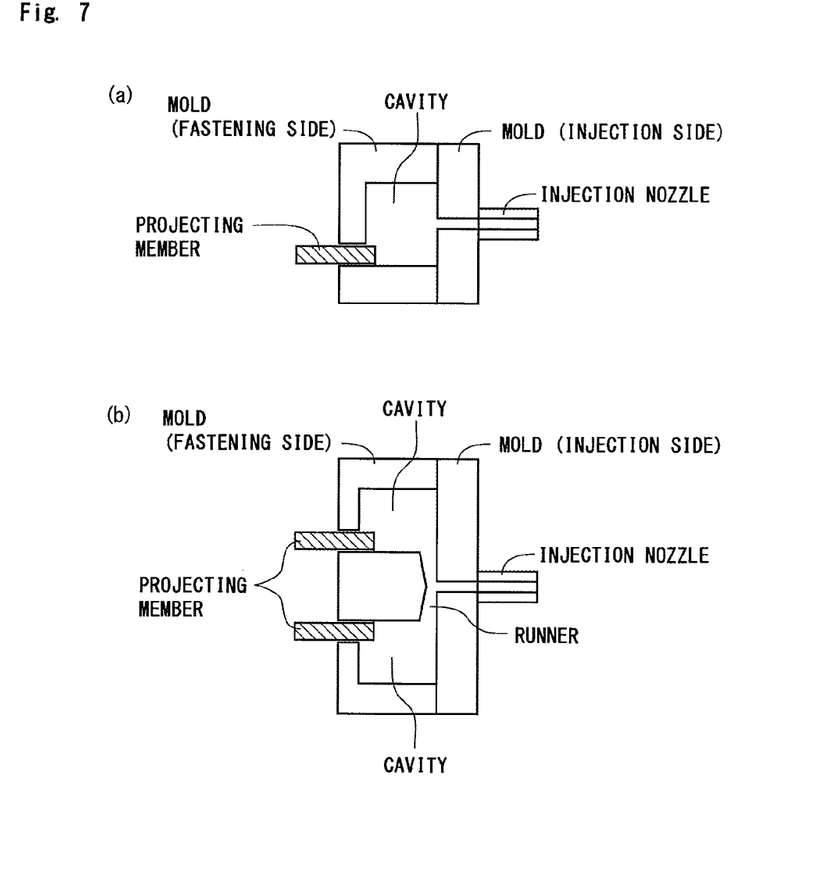
FIG. 7 It is a schematic view of embodiments of the pushing portion where the projecting member is pushed into the side surface of the cavity.

It is desired that the position of the pushing portion in the side surface is at the center of the side surface so that the pressure can be exerted uniformly over the whole resin block. Not being limited thereto only, however, the pushing potion may be formed at an end of the side surface as shown in FIG. 7(*a*).

Moreover, to produce a plurality of resin blocks at one time, there can be used a mold having a plurality of cavities. In this case, in principle, the pushing operation is executed by using the projecting member for each of the cavities [FIG. 7(*b*)].

It is desired that the side surface in the cavity where the pushing portion is present is just opposite to the side surface where there is a port for filling the molten thermoplastic resin composition from the standpoint of easy design of the apparatus and simplicity of the mechanisms.

The pressure exerted on the resin block at the time of pushing in is, usually, not less than 10 MPa and, preferably, 100 to 1000 MPa. The pressure can be controlled by adjusting the compressive stress of the projecting compression mechanism. In a simple manner, however, the pressure can be controlled relying on the contact area of the projecting member and the pushing distance. If the pressure is too small, the occurrence of voids cannot often be suppressed. If the pressure is too large, on the other hand, the formed body will be broken, which is not desirable. Further, a desired volume of pushing in is 0.1 to 10% and, more preferably, 0.5 to 5% of the volume of the cavity.

The timing for starting the pushing operation is after the start of the step of exerting the holding pressure that follows the step of injection and after the thermoplastic resin has started solidifying but before it is completely solidified. The thermoplastic resin composition does not solidify as a whole at the same time but, usually, solidifies starting from the surface of the mold, from a thin portion of the resin block or from a portion of the mold where the temperature is low. The timing for starting the pushing operation varies depending on the thermoplastic resin composition that is used, structure of the mold or the gate seal, and cannot be exclusively specified. Therefore, the timing thereof is determined by trial and error. Usually, the timing for starting the pushing operation is after 1 to 120 seconds have passed from when the resin was filled.

The temperature of the cavity portion (mold) during the pushing operation differs depending on the thermoplastic resin composition that is used, and may be suitably selected. Usually, however, the mold temperature is set to be about 100° C. to about 300° C. lower than the fluidizing temperature of the thermoplastic resin composition.

The pressure is exerted on the whole resin block due to the pushing operation by using the projecting member. Here, if the projecting member is pushed into the flat side surface, then a dent is formed in the side surface of the resin block that is obtained which may not be often desirable for the subsequent milling operation (FIG. 1). To avoid this, one side surface in the cavity of the mold is protruded outwardly of the cavity. The thermoplastic resin composition is then filled and the pressure is exerted thereon. Thereafter, at a moment when the outer surface of the resin block including the protruded portion starts solidifying, the projecting member is pushed onto the protruded portion from the outer side to exert the pressure. Then the protruded portion is pushed in, and the resin block is prepared finally having a flat side surface (FIG. 2).

The compression operation for the thermoplastic resin composition before it is completely solidified is not limited to the pushing operation by pushing the projecting member into the side surface of the cavity.

It is also a preferred embodiment to separately provide a compression chamber having a pushing portion that has a space continuous to the interior of the cavity, and push the projecting member into one side surface of the compression chamber that has the pushing portion, over a contact area of not more than 50% on the basis of the area of the whole side surface. In the embodiment of providing the compression chamber that has the pushing portion, the resin block is not directly pushed in and, therefore, no dent is formed in the resin block, offering an advantage in the subsequent milling work.

Figure 5:
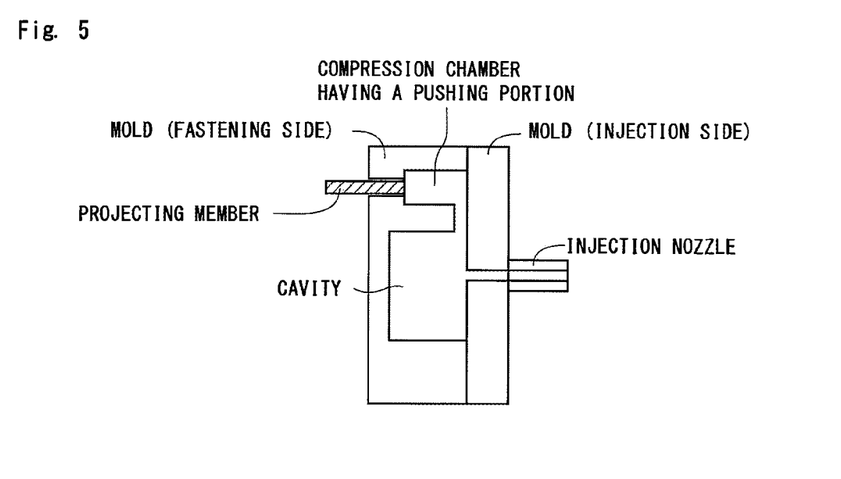
FIG. 5 It is a schematic view of an embodiment that executes the pushing operation for a compression chamber that has a separately provided pushing portion being linked to the cavity.
Figure 6:
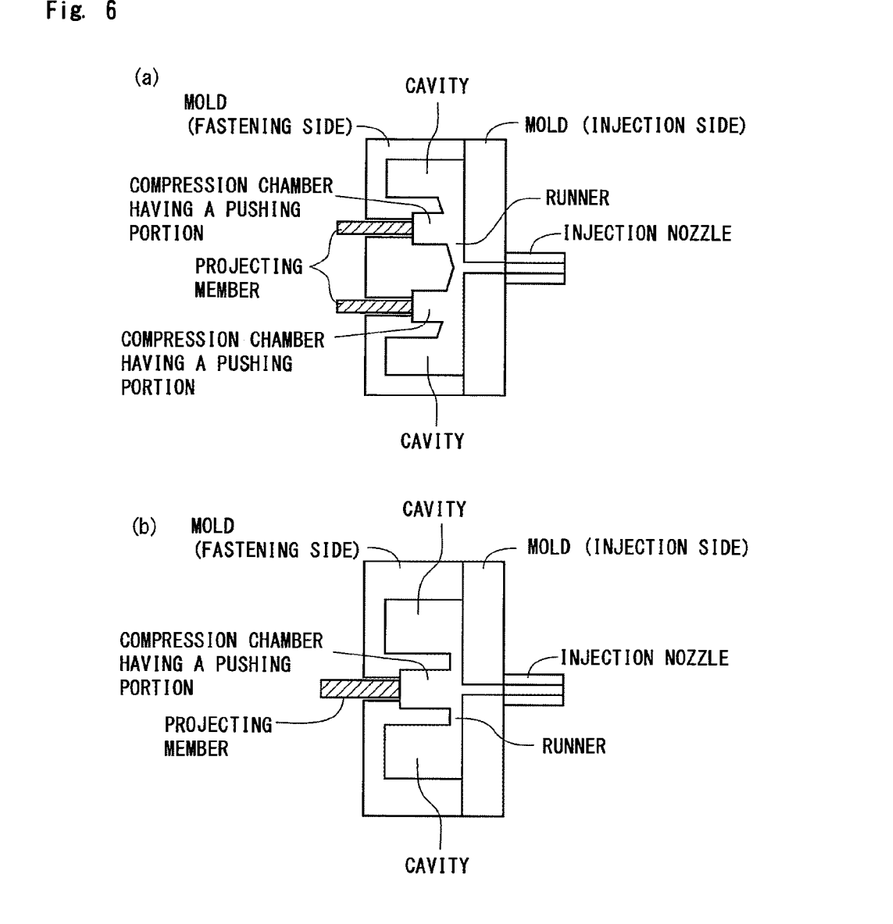
FIG. 6 It is a schematic view of an embodiment that executes the pushing operation for the compression chamber that has the pushing portion in the runner portion.

The compression chamber having the pushing portion, as shown in FIG. 5, may be provided at the back of the cavity or may be provided in the runner portion through which the molten thermoplastic resin composition is fed into the cavity [FIG. 6(*a*), (*b*)]. The volume of the compression chamber having the pushing portion must be 0.2 to 80% of the volume of the cavity. By setting the volume to be not less than 0.2%, the occurrence of voids can be suppressed to a sufficient degree. By setting the volume to be not more than 80%, the thermoplastic resin composition is prevented from being used excessively. From this point of view, the volume should, preferably, be 1.0 to 30%. When there is used a mold having a plurality of cavities, the volume of the cavity stands for the total volume of the cavities, and the volume of the compression chamber having the pushing portion stands for the total volume of the compression chambers that have the pushing portion. That is, the total volume of the compression chambers having the pushing portion must be set to be 0.2 to 80% of the total volume of the cavities that are linked together.

When there is used a mold having a plurality of cavities, it is desired that the compression chamber having the pushing portion is provided for each of the cavities. It is, however, also allowable to provide a compression unit having the pushing portion that is linked in common to the plurality of cavities, and execute the pushing operation at one place for the plurality of cavities [FIG. 6 (*b*)]. When the pushing operation is executed at one place for the plurality of cavities, the volume of the compression chamber having the pushing portion is 0.2% to 80% of the total volume of the cavities.

When there are used the plurality of cavities, their sizes and shapes may be different from each other but should, desirably, be the same from the standpoint of attaining a homogeneous injection molding.

There is no limitation on the shape of the runner. When the compression chamber having the pushing portion is arranged in the runner portion or in the back of the cavity, it is desired to adjust the size and shape of the runner, such as increasing the size of the runner and shortening the flow passage so that, during the compression operation, the thermoplastic resin composition present in the flow passage between the cavity and the compression chamber having the pushing portion will not be completely solidified but still maintains fluidity.

[Step of Cooling and Step of Taking Out Formed Body]

In the step of cooling and the step of taking out the formed body in the production process of the present invention, the resin block in the cavity is sufficiently cooled down to an extent that it will not be deformed by the pressure exerted from the exterior and, thereafter, the mold is opened to take out the formed body. The mold is then closed to repeat the cycle of forming.

Any known methods, apparatus and equipment can be used for cooling and for taking out the formed body. Qualities of the formed body can be affected by various conditions such as the temperature of the mold, distribution of the temperature, cooling time, holding pressure and design of the take-out mechanism. Therefore, optimum factors should be suitably selected and set in determining the conditions. The temperature of the mold in the step of cooling may be the same as, or may be different from, the temperature of the mold in the preceding step of exerting the holding pressure and the step of compression.

[Other Steps]

The process for producing the resin block of the present invention may include any other steps. For instance, it may include the steps of drying the starting materials, pre-heating the starting materials, venting and purging. As required, furthermore, the process may further include the steps of treating the formed body, such as the steps of regeneration, polishing, heat treatment, milling, gate milling, machining, junction and adhesion.

In obtaining the body from the resin block of the present invention through the milling work, there is no particular limitation on the method of fastening the resin block to the milling machine. A general fastening method consists of fastening the resin block to the body of the milling machine or to the jig for fixing to the milling machine by adhesion, insertion or by using screws. Or, a fastening pin may be linked to the resin block by adhesion, insertion or by screw, and the fastening pin may then be fastened to the body of the milling machine or to the jig for fixing to the milling machine. There is no particular limitation on the kind and material of the fastening pin, and there can be used pins made of metals like stainless steel, aluminum or brass, or resins or ceramics. There is no particular limitation on the adhesive, either, and there can be used any commercially available materials such as those of the types of isocyanate, epoxy, urethane, silicone or acrylics.

[Injection-molding Apparatus and Mold]

As the injection-molding apparatus used for producing the resin block, there can be used any known apparatus, mechanism or commercially available apparatus except the pushing mechanism that utilizes the projecting member before the thermoplastic resin composition is completely solidified.

That is, the injection-molding apparatus basically comprises an injection unit that heats and melts the thermoplastic resin composition, injects it into the mold, and exerts the pressure on it; a mold; and a mold-fastening unit that opens and closes the mold, and takes out the formed body therefrom.

The injection unit is constituted by basic components such as a starting material feed unit, a heater, a cylinder, a screw and a motor. An injection unit that has been known per se. can be just used. The mold-fastening unit is for opening and closing the mold, and for taking out the formed body therefrom. The mold-fastening unit comprises the components known per se.

The mold used for the process for producing the resin block of the present invention is designed to meet the shape of the resin block that is desired. The mold according to the present invention is basically designed:
1) In a structure which enables the projecting member to be pushed into one side surface of the cavity; or
2) In a structure which enables the projecting member to be pushed into the side surface of the compression chamber with the pushing portion that has a space continuous to the interior of the cavity.

The shape, structure, mechanism and the like of the mold can be arbitrarily designed so far as it has the above-mentioned basic structure. Further, the mold may have a plurality of cavities such that a plurality of resin blocks can be produced through the one time of forming. A representative mold has a protruded portion on one side surface in the cavity, the protruded portion protruding outwards of the cavity (see FIG. 2).

As for designing the cavity block, sprue, runner, hot runner, gate, take-out mechanism, ejector pin, stripper plate, temperature-adjusting mechanism, mold base, slide core, angular pin, guide pin, guide bush, return pin, support pin, coil spring, material of the mold, surface treatment, etc., it is recommended that they are selected and designed to work in a suitable and optimum manner under the production conditions.

By employing the production process of the present invention, it is allowed to easily produce, without permitting voids to occur, a resin block of a large size which permitted voids to easily occur with the conventional processes. Therefore, the present invention is more effective in producing the resin blocks having volumes of not less than 100 $mm^3$, more preferably, not less than 2,000 $mm^3$ and, particularly preferably, not less than 10,000 $mm^3$. If easiness of production of the resin blocks and uniformity in the forming temperature are brought into consideration, it is desired that the volumes of the resin blocks are, preferably, not more than 1,000,000 $mm^3$, more preferably, not more than 200,000 $mm^3$ and, particularly preferably, not more than 100,000 $mm^3$.

If mentioned concerning the conditions of injection molding, the occurrence of voids can be suppressed, generally, by sufficiently compressing the resin composition by elevating the injection pressure, elevating the mold temperature to decrease a temperature differential of the resin when it is cooled, lowering the cylinder temperature to decrease a temperature differential of the resin when it is cooled, elevating the holding pressure to lengthen the duration of the holding pressure, increasing the metering, increasing the cushioning amount, and increasing or decreasing the injection rate. If mentioned concerning the mold designing, the occurrence of voids can be suppressed by forming the formed body in a uniform thickness, increasing the size of the sprue and runner, increasing the size of the gate and shortening the length thereof, forming the gate near the thickest portion, and increasing the number of the gates.

By employing these known methods, the occurrence of voids can be suppressed to some extent. However, every condition could affect other conditions. Therefore, the occurrence of voids cannot be prevented to a sufficient degree no matter how these conditions are optimized.

[Use of the Resin Block]

The resin block of the present invention has a large mechanical strength, and can be preferably used, particularly, as a resin material for dental use through the milling work. Concretely, the resin block can be favorably used as a prosthetic for restoring the crown, such as inlay, onlay, crown, bridge and the like, and as denture, denture base, artificial teeth, implant fixture, abutment, upper part structure, material for building abutment, and the like.

[Working the Resin Block]

Described below is a method of preparing a prosthetic by using the resin block of the present invention.

First, a dentist forms an abutment in the oral cavity of a patient. For example, a tooth is ground to form the abutment. Next, the dentist obtains an impression of the abutment, neighboring teeth, opposing teeth, etc. The impression is obtained by using an alginate type impression material, a silicone type impression material or by using a digital impression apparatus. Thereafter, a dental technician or the dentist prepares a clay model based on the obtained impression, and digitizes the shape of the clay model by using a scanning machine. Or, a digital model is prepared from the data obtained from the digital impression.

Next, digital data of a prosthetic is obtained based on the measured data and by using a design software. Based on the digital data of the prosthetic, there are obtained digital data for milling by using a milling machine. Preferably, at this moment, make sure on the software that the resin block has a size large enough for preparing the prosthetic.

Thereafter, the resin block for dental milling work of the invention is set to a milling machine and is cut. After the milling work has been finished by the milling machine, the sprue portion is separated away that might be remaining on the resin block for dental milling work. After having corrected the form and after having polished, the inner surface of the prosthetic, as required, is subjected to a pretreatment (roughening by the sand-blasting or the like). As required, further, the thus prepared prosthetic is subjected on inner surface thereof to a pretreatment (application of a primer or the like) and is, thereafter, adhered to the abutment in the oral cavity of the patient.

The milling work is done by using a milling machine (CAM, milling machine). It is desired to use a dental milling machine placed in the market. The milling work requires a milling tool (bar) and a software for the milling work (CAM). The CAM software works to control the movement of the milling tool and the movement of the resin block that is fastened via a fastening tool. Representative parameters include position data, feeding speed and revolving speed. As the milling tool, it is desired to use a general dental milling bar. As a countermeasure against the abrasion, it is desired that the milling tool has a coating such as diamond coating. In general, the milling bar consists of a combination of a plurality of milling bars that are selectively used depending on the degree of milling, such as rough milling, intermediate milling, fine milling, etc. If simply described, the crown is roughly formed by using the bar for rough milling (e.g., 2 mm in diameter) and, thereafter, the surface shape is smoothed by using the bar for fine milling (e.g., 0.8 mm in diameter), and a fine structure such as of an occlusal surface is expressed.

In milling the resin block for dental cut working, the prosthetic formed by the milling work must remain linked to the uncut portion until the milling work is finished by the milling machine. For this purpose, the prosthetic is provided with the sprue which links it to the uncut portion. In case voids are contained in the sprue, then the prosthetic may split off during the forming work, which is not desirable.

EXAMPLES

The present invention will now be concretely described by means of Examples and Comparative Examples to which only, however, the invention is in no way limited. Moreover, it does not mean that the combinations of features described in Examples are all essential for solving the problems of the present invention.

Described below are the testing methods employed in the following Examples and Comparative Examples.

Measuring the Voids:

An X-ray image of the resin block was photographed by using an X-ray inspection apparatus μ nRay 7600 (manufactured by Matsusada Precision Co.). The tube voltage was set at 90 kV, and a contrast value was adjusted to be an optimum value for viewing voids. The photographed X-ray image was inspected to examine the presence, number and longest diameters of voids.

Evaluating the Appearance and Measuring the Strength of the Crown Form Prosthetic:

A resin block for milling work was prepared by adhering, as the fastening fitting, an aluminum pin onto a surface having a minimum area of the resin block by using a cyanoacrylate type instant adhesive. There were provided CAD data and a milling program for milling the prosthetic for restoring the crown No. 7 of the left lower jaw. By using the CAD software, a crown form was designed based on a crown form model tooth and a model tool for forming abutment for full-cast crown (both manufactured by Nisshin). By using the CAM software, a milling program was prepared based on the CAD data that are obtained. The sprue was studded on the mesial surface and was formed in a conical shape 2.5 mm in diameter. The resin block for milling work was fastened, via a fastening pin, to a milling machine (DWX-50, manufactured by Roland DG) and was cut. As the milling bars, there were used the one for rough milling of a diameter of φ 2.0 mm and the one for fine milling of a diameter of φ 0.8 mm (both manufactured by YAMAHACHI DENTAL MFG., Co.). The milling bar was revolved at 30,000 rpm. The sprue was cut by using a diamond disc point while traces of the sprue were removed by using a Carborundum point, and a crown form prosthetic was thus obtained. The appearance at this moment was evaluated with the eye. The crown form prosthetic was set to the above-mentioned model tooth forming the abutment, a steel ball of a diameter of φ 10 mm was placed on the occlusal surface of the prosthetic, and a compression test was conducted by using a universal testing machine (Autograph AG-50KN, manufactured by SHIMADZU) at a crosshead speed of 1.0 mm/min. A stress value [N] was measured at a moment when the crown form prosthetic was broken.

Production Example 1

100 Parts by weight of VESTAKEEPM2G (aromatic polyetheretherketone, melting point 340° C., produced by Ebonic Co.) and 66 parts by mass of silica (spherical, volume average particle size 0.2 microns, treated with γ-methacryloyloxypropyltrimethoxysilane) were mixed together in a mixer. The mixture thereof was pre-dried in a drier at 100° C. for 10 hours and was melt-kneaded by using a twin screw extruder. The melt-kneaded material was then pelletized into a size of about 3 mm to prepare a composite resin composition A.

Production Example 2

100 Parts by weight of VESTAKEEPM2G (aromatic polyetheretherketone, melting point 340° C., produced by Ebonic Co.), 43 parts by mass of silica (spherical, volume average particle size 1.0 micron, treated with γ-methacryloyloxypropyltrimethoxysilane) and 10 parts by mass of titanium oxide (spherical, volume average particle size 0.3 microns) were mixed together in a mixer. The mixture thereof was pre-dried in the drier at 100° C. for 10 hours and was melt-kneaded by using the twin screw extruder. The melt-kneaded material was then pelletized into a size of about 3 mm to prepare a composite resin composition B.

Production Example 3

100 Parts by weight of VESTAKEEP1000G (aromatic polyetheretherketone, melting point 340° C., produced by Evonik) and 150 parts by mass of silica (spherical, volume average particle size 1.0 microns, treated with γ-methacryloyloxypropyltrimethoxysilane) were mixed together in a mixer. The mixture thereof was pre-dried in the drier at 100° C. for 10 hours and was melt-kneaded by using the twin screw extruder. The melt-kneaded material was then pelletized into a size of about 3 mm to prepare a composite resin composition C.

Reference Example 1

On an injection-molding machine, SE18DUZ, (manufactured by Sumitomo Heavy Industries, Ltd.), there was installed a mold unit having a cavity measuring 12×14×18 mm and a protruded portion measuring φ6×1 mm at the central portion of the surface on the side opposite to the surface that is in contact with the injection nozzle and, further, having a mechanism for pushing a projecting pin having an end of a diameter of φ6 mm. VICTREXPEEK450G (aromatic polyetheretherketone, melting point 340° C.; produced by Victrex) was thrown into a hopper equipped with a pre-drying machine, and was injected and filled under the conditions of a forming temperature (cylinder temperature) of 360 to 400° C., a fluidizing temperature of 360° C., a mold temperature of 180° C., an injection pressure of 150 MPa and an injection rate of 50 mm/sec. After 20 seconds have passed from when the resin was filled, the pushing mechanism was moved by 1.0 mm from the end of the protruded portion toward the surface with which the injection nozzle was in contact while exerting the holding pressure of 150 MPa to thereby push the resin. The contact area of the projecting member was 28 mm$^2$ which was 11% of the area of the side surface (14×18 mm). After the mold was cooled for 300 seconds, the mold unit was opened and the resin block was taken out. The resin block was inspected with the X-rays, and there was not found any void having the longest diameter of not less than 0.2 mm. The crown form prosthetic obtained through the milling work exhibited favorable appearance without any non-uniform portions. The stress load test showed that the crown form prosthetic was not broken despite a load of not less than 2000 N was exerted. However, an indentation due to the steel ball of ϕ10 mm was formed in the surface of the crown form prosthetic.

Example 1

On the injection-molding machine, SE18DUZ, (manufactured by Sumitomo Heavy Industries, Ltd.), there was installed a mold unit having a cavity measuring 12×14×18 mm and a protruded portion measuring ϕ6×2 mm at the central portion of the surface on the side opposite to the surface that is in contact with the injection nozzle and, further, having a mechanism for pushing a projecting pin having an end of a diameter of ϕ6 mm. VESTAKEEPMC4420G (aromatic polyetheretherketone, melting point 340° C., titanium oxide filling rate 20 wt %; produced by Evonik) was thrown into the hopper equipped with the pre-drying machine, and was injected and filled under the conditions of a forming temperature (cylinder temperature) of 360 to 400° C., a fluidizing temperature of 360'C, a mold temperature of 180° C., an injection pressure of 180 MPa and an injection rate of 50 mm/sec. After 40 seconds have passed from when the resin was filled, the pushing mechanism was moved by 2.0 mm from the end of the protruded portion toward the surface with which the injection nozzle was in contact while exerting the holding pressure of 160 MPa to thereby push the resin. The contact area of the projecting member was 28 mm$^2$ which was 11% of the area of the side surface (14×18 mm). After the mold was cooled for 300 seconds, the mold unit was opened and the resin block was taken out. The resin block was inspected with the X-rays, and there was not found any void having the longest diameter of not less than 0.2 mm. The crown form prosthetic obtained through the milling work exhibited favorable appearance without any non-uniform portions. The stress load test showed that the crown form prosthetic was not broken despite a load of not less than 2000 N was exerted. No indentation was found, either.

Example 2

On an injection-molding machine, LA40, (manufactured by Sodick), there was installed a mold unit having a cavity measuring 12×14×18 mm and a protruded portion measuring ϕ6×2 mm at the central portion of the surface on the side opposite to the surface that is in contact with the injection nozzle and, further, having a mechanism for pushing a projecting pin having an end of a diameter of ϕ56 mm. The composite resin composition A was thrown into the hopper equipped with the pre-drying machine, and was injected and filled under the conditions of a forming temperature (cylinder temperature) of 360 to 400° C., a fluidizing temperature of 360° C., a mold temperature of 190° C., an injection pressure of 200 MPa and an injection rate of 50 mm/sec. After 60 seconds have passed from when the resin was filled, the pushing mechanism was moved by 2.0 mm from the end of the protruded portion toward the surface with which the injection nozzle was in contact while exerting the holding pressure of 200 MPa to thereby push the resin. The contact area of the projecting member was 28 mm$^2$ which was 11% of the area of the side surface (14×18 mm). After the mold was cooled for 300 seconds, the mold unit was opened and the resin block was taken out. The resin block was inspected with the X-rays, and there was not found any void having the longest diameter of not less than 0.2 mm. The crown form prosthetic obtained through the milling work exhibited favorable appearance without any non-uniform portions. The stress load test showed that the crown form prosthetic was not broken despite a load of not less than 2000 N was exerted. No indentation was found, either.

Example 3

On an injection-molding machine, GL60, (manufactured by Sodick), there was installed a mold unit having a cavity measuring 16×19×39 mm and a protruded portion measuring ϕ6×4 mm at the central portion of the surface on the side opposite to the surface that is in contact with the injection nozzle and, further, having a mechanism for pushing a projecting pin having an end of a diameter of ϕ6 mm. The composite resin composition B was thrown into the hopper equipped with the pre-drying machine, and was injected and filled under the conditions of a forming temperature (cylinder temperature) of 360 to 400° C., a fluidizing temperature of 360° C., a mold temperature of 200° C., an injection pressure of 350 MPa and an injection rate of 50 mm/sec. After 80 seconds have passed from when the resin was filled, the pushing mechanism was moved by 4.00 mm from the end of the protruded portion toward the surface with which the injection nozzle was in contact while exerting the holding pressure of 350 MPa to thereby push the resin. The contact area of the projecting member was 28 mm$^2$ which was 4% of the area of the side surface (19×39 mm). After the mold was cooled for 300 seconds, the mold unit was opened and the resin block was taken out. The resin block was inspected with the X-rays, and there was not found any void having the longest diameter of not less than 0.2 mm. The crown form prosthetic obtained through the milling work exhibited favorable appearance without any non-uniform portions. The stress load test showed that the crown form prosthetic was not broken despite a load of not less than 2000 N was exerted. No indentation was found, either.

Example 4

On an injection-molding machine, J55E, (manufactured by The Japan Steel Works, LTD.), there was installed a mold unit having a cavity measuring 16×19×39 mm and a protruded portion measuring ϕ6×5 mm at the central portion of the surface on the side opposite to the surface that was in contact with the injection nozzle and, further, having a mechanism for pushing a projecting pin having an end of a diameter of ϕ6 mm. The composite resin composition C was thrown into the hopper equipped with the pre-drying machine, and was injected and filled under the conditions of a forming temperature (cylinder temperature) of 360 to 400° C., a fluidizing temperature of 360° C., a mold temperature of 200° C., an injection pressure of 250 MPa and an injection rate of 100 mm/sec. After 50 seconds have passed from when the resin was filled, the pushing mechanism was moved by 5.00 mm from the end of the protruded portion toward the surface with which the injection nozzle was in contact while exerting the holding pressure of 250 MPa to thereby push the resin. The contact area of the projecting member was 28 mm$^2$ which was 4% of the area of the side surface (19×39 mm). After the mold was cooled for 300 seconds, the mold unit was opened and the resin block was taken out. The resin block was inspected with the X-rays, and there was not found any void having the longest diameter of not less than 0.2 mm. The crown form prosthetic obtained through the milling work exhibited favorable appearance without any non-uniform portions. The stress load test showed that the crown form prosthetic was not broken despite a load of not less than 2000 N was exerted. No indentation was found, either.

Comparative Example 1

On an injection-molding machine, J55E, (manufactured by The Japan Steel Works, LTD.), there was installed a mold unit having a cavity measuring 16×19×39 mm. The composite resin composition C was thrown into the hopper equipped with the pre-drying machine, and was injected and filled under the conditions of a forming temperature (cylinder temperature) of 360 to 400° C., a fluidizing temperature of 360° C., a mold temperature of 200° C., an injection pressure of 250 MPa and an injection rate of 100 mm/sec. While exerting the holding pressure of 250 MPa, the mold was cooled for 300 seconds and, thereafter, the mold unit was opened to take out and the resin block. The resin block was inspected with the X-rays, and there was found a void having the longest diameter of 9.2 mm in the central portion. The crown form prosthetic obtained through the milling work exhibited a pore exposed in the occlusal surface. As a result of the stress load test, the crown form prosthetic was broken under a stress load of 817 N.

Comparative Example 2

On the injection-molding machine, GL60, (manufactured by Sodick), there was installed a mold unit having a cavity measuring 16×19×39 mm and a mechanism having a protruding area capable of executing the compression over a surface of 16×19 mm which was 100% of the surface of the cavity on the side opposite to the surface in which the injection nozzle was in contact. The composite resin composition B was thrown into the hopper equipped with the pre-drying machine, and was injected and filled under the conditions of a forming temperature (cylinder temperature) of 360 to 400° C., a fluidizing temperature of 360° C., a mold temperature of 200° C., an injection pressure of 350 MPa and an injection rate of 50 mm/sec. The operation was so programmed that after 80 seconds have passed from when the resin was filled, the pushing mechanism was to be moved by 4.00 mm from the end of the protruded portion toward the surface with which the injection nozzle was in contact while exerting the holding pressure of 350 MPa. Though it was attempted to push the resin in, however, the protruding surface came into a halt before the resin was completely pushed in. The mold unit was cooled for 300 seconds, and the mold unit was opened to take out the resin block. The resin block was inspected with the X-rays, and there was found a void having the longest diameter of 6.7 mm in the direction of the long axis in the central portion. The crown form prosthetic obtained through the milling work exhibited a pore exposed in the occlusal surface. As a result of the stress load test, the crown form prosthetic was broken under a stress load of 871 N.

The invention claimed is:

1. A process for producing a resin block that contains a thermoplastic resin and inorganic particles, that does not contain any void whose length is not less than 1.0 mm, that has a thick portion of a thickness of at least 5 mm, and that can be used as a material for producing a dental prosthetic through milling work:
    by providing a thermoplastic resin composition that contains a thermoplastic resin having a fluidizing temperature in a range of 310 to 500° C. and at least one kind of inorganic oxide particles selected from the group consisting of silica particles, silica composite particles of silica and other metal oxides, titania particles, and titania composite particles of titania and other metal oxides in an amount of 30 to 150 parts by mass per 100 parts by mass of the thermoplastic resin, and comprising the steps of:
    injecting and filling a melt of said thermoplastic resin composition in a cavity of an injection-molding machine that has a projection mechanism;
    exerting a pressure on the thermoplastic resin composition;
    pushing a projecting member into one side surface of the cavity filled with the thermoplastic resin composition over a contact area of not more than 50% on the basis of the contact area of the whole one side surface before the thermoplastic resin composition is completely solidified; and
    taking out the thermoplastic resin composition after it has been cooled down.

2. The process for producing the resin block according to claim 1, wherein a portion in one side surface of the cavity filled with the thermoplastic resin composition with which the projecting member comes in contact is formed being protruded toward an outer side of the cavity, and the projecting member is pushed so that the one side surface of the cavity filled with the thermoplastic resin composition becomes nearly flat.

3. A process for producing a resin block that contains a thermoplastic resin and inorganic particles, that does not contain any void whose length is not less than 1.0 mm, that has a thick portion of a thickness of at least 5 mm, and that can be used as a material for producing a dental prosthetic through milling work:
    by providing a thermoplastic resin composition that contains a thermoplastic resin having a fluidizing temperature in a range of 310 to 500° C. and at least one kind of inorganic oxide particles selected from the group consisting of silica particles, silica composite particles of silica and other metal oxides, titania particles, and titania composite particles of titania and other metal oxides in an amount of 30 to 150 parts by mass per 100 parts by mass of the thermoplastic resin, and comprising the steps of:
    injecting and filling a melt of said thermoplastic resin composition in a cavity of an injection-molding machine that has a projection mechanism;
    exerting a pressure on the thermoplastic resin composition;
    pushing a projecting member into one side surface of a compression chamber that has a pushing portion, over a contact area of not more than 50% on the basis of the contact area of said whole one side surface before the thermoplastic resin composition is completely solidified, the compression chamber having a volume which is 0.2 to 80% the volume of the cavity and, further, having a space continuous to an interior of the cavity; and
    taking out the thermoplastic resin composition after it has been cooled down.

4. The process for producing the resin block according to claim 1, wherein the thermoplastic resin is a crystalline thermoplastic resin.

5. The process for producing the resin block according to claim 1, wherein the thick portion has a thickness of 10 to 50 mm.

6. The process for producing the resin block according to claim 1, wherein the resin block does not contain any void whose length is not less than 0.2 mm.

7. The process for producing the resin block according to claim 1, wherein the milling work is executed by using a CAD/CAM (computer aided design•manufacturing) system.

\* \* \* \* \*